(12) United States Patent
Weber et al.

(10) Patent No.: US 11,520,847 B2
(45) Date of Patent: Dec. 6, 2022

(54) LEARNING INTERPRETABLE STRATEGIES IN THE PRESENCE OF EXISTING DOMAIN KNOWLEDGE

(71) Applicant: International Business Machines Corporation, Armonk, NY (US)

(72) Inventors: Daniel Weber, Oronoco, MN (US); David A. Christenson, Fergus Falls, MN (US); Nathaniel E. Rykal, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 261 days.

(21) Appl. No.: 16/736,992

(22) Filed: Jan. 8, 2020

(65) Prior Publication Data

US 2021/0209186 A1    Jul. 8, 2021

(51) Int. Cl.
  *G06F 16/30*    (2019.01)
  *G06F 16/9538*  (2019.01)
  *G06F 16/93*    (2019.01)
  *G16H 50/70*    (2018.01)
  *G16H 70/00*    (2018.01)
  *G06F 16/951*   (2019.01)

(52) U.S. Cl.
  CPC .......... *G06F 16/9538* (2019.01); *G06F 16/93* (2019.01); *G06F 16/951* (2019.01); *G16H 50/70* (2018.01); *G16H 70/00* (2018.01)

(58) Field of Classification Search
  CPC ..... G06F 16/9538; G06F 16/93; G06F 16/951
  See application file for complete search history.

(56) References Cited

U.S. PATENT DOCUMENTS

| 2012/0290612 | A1* | 11/2012 | Ritoe ............... | G06F 16/9537 707/770 |
| 2013/0218596 | A1* | 8/2013 | Gome ............... | G06Q 10/06 705/3 |
| 2014/0310255 | A1* | 10/2014 | Cardell ............. | G06F 16/5866 707/706 |

(Continued)

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Khanh B Pham
(74) *Attorney, Agent, or Firm* — Stephen J. Walder, Jr.; Aaron Pontikos

(57) ABSTRACT

A mechanism is provided in a data processing system to implement a medical concept searching engine for improving searches of medical concepts based on an index model. The mechanism generates a concept index model data structure that records medical concepts and corresponding numbers of instances of the medical concepts in the corpus of documents. Responsive to receiving a search request from a user, the medical concept searching engine identifies at least one medical concept in the search request and one or more related medical concepts that are related to the at least one medical concept based on an ontology data structure. The medical concept searching engine generates a bubble graph user interface comprising a plurality of bubbles corresponding to the at least one medical concept and the one or more related medical concepts.

20 Claims, 6 Drawing Sheets

(56) References Cited

U.S. PATENT DOCUMENTS

| | | | | |
|---|---|---|---|---|
| 2016/0019356 A1* | 1/2016 | Martin | ............... | G16B 50/10 |
| | | | | 705/2 |
| 2016/0203281 A1* | 7/2016 | Zalis | ............... | G16H 10/60 |
| | | | | 705/3 |
| 2020/0176098 A1* | 6/2020 | Lucas | ............... | G16H 15/00 |

OTHER PUBLICATIONS

Yuan, Michael J., "Watson and healthcare, How natural language processing and semantic search could revolutionize clinical decision support", IBM Corporation, IBM developerWorks, http://www.IBM.com/developerworks/industry/library/ind-watson/, Apr. 12, 2011, 14 pages.

* cited by examiner

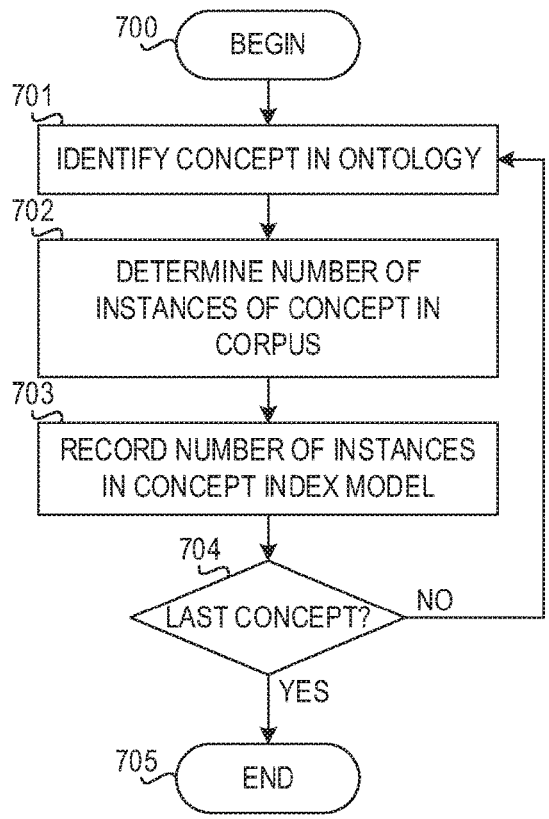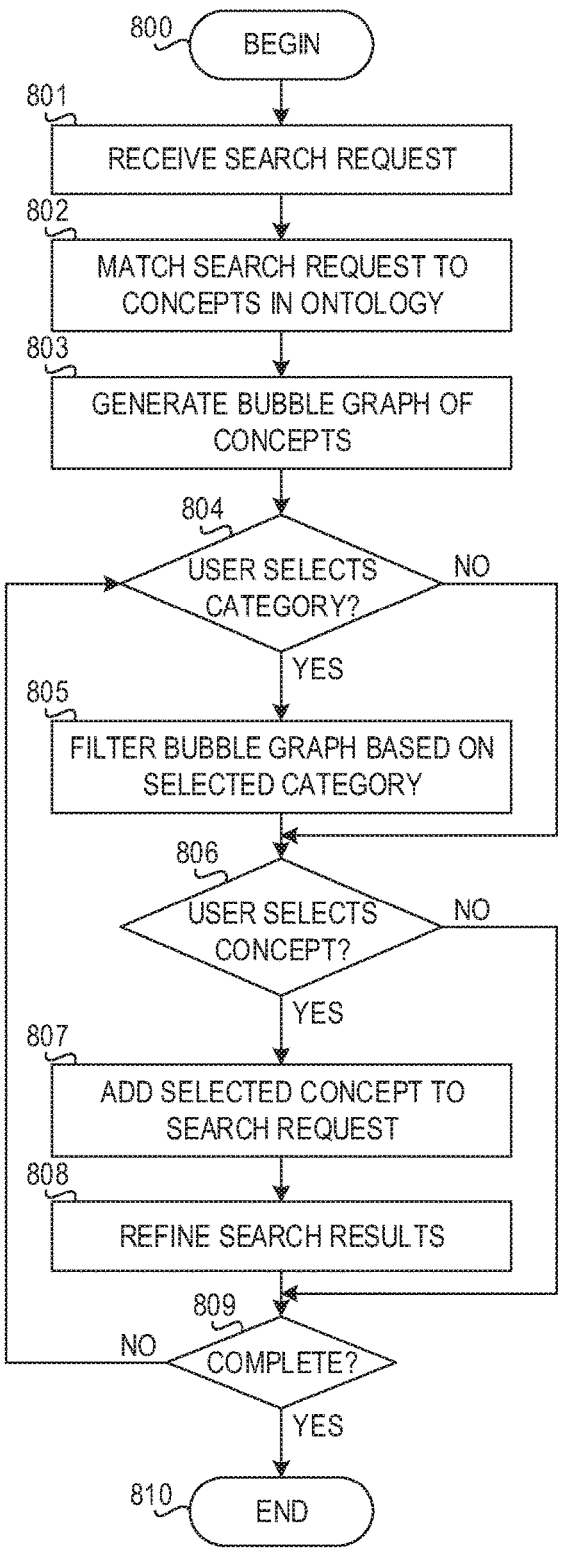

LEARNING INTERPRETABLE STRATEGIES IN THE PRESENCE OF EXISTING DOMAIN KNOWLEDGE

BACKGROUND

The present application relates generally to an improved data processing apparatus and method and more specifically to mechanisms for improving searches of medical concepts based on an index model.

A search engine is a software system that is designed to carry out a search, which means to search a corpus of documents in a systematic way for particular information specified in a textual search query. The search results are generally presented in a line of results, often referred to as search engine results pages (SERPs). The information may be a mix of links to documents, images, videos, infographics, articles, research papers, and other types of files. Some search engines also mine data available in databases or open directories.

Search engine optimization indexing collects, parses, and stores data to facilitate fast and accurate information retrieval. Index design incorporates interdisciplinary concepts from linguistics, cognitive psychology, mathematics, informatics, and computer science. Popular search engines focus on full-text indexing of online, natural language documents. Media types such as video, audio, and graphics may also be searchable.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a medical concept searching engine for improving searches of medical concepts based on an index model. The method comprises generating a concept index model data structure that records medical concepts and corresponding numbers of instances of the medical concepts in the corpus of documents. The method further comprises identifying, by the medical concept searching engine, at least one medical concept in a search request. The method further comprises identifying, by the medical concept searching engine, one or more related medical concepts that are related to at least one medical concept based on an ontology data structure. The method further comprises generating, by the medical concept searching engine, a bubble graph user interface comprising a plurality of bubbles corresponding to the at least one medical concept and the one or more related medical concepts. A size of each bubble in the bubble graph user interface is proportional to an impact of the corresponding medical concept on the search results. Each bubble in the bubble graph user interface has a selection control that is selectable by the user to add the corresponding medical concept to the search request. The method further comprises presenting, by the medical concept searching engine, the bubble graph user interface to the user.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 7 is a flowchart illustrating operation of a concept indexing engine in accordance with an illustrative embodiment; and FIG. 8 is a flowchart illustrating operation of a concept search engine in accordance with an illustrative embodiment.

DETAILED DESCRIPTION

Figure 1:
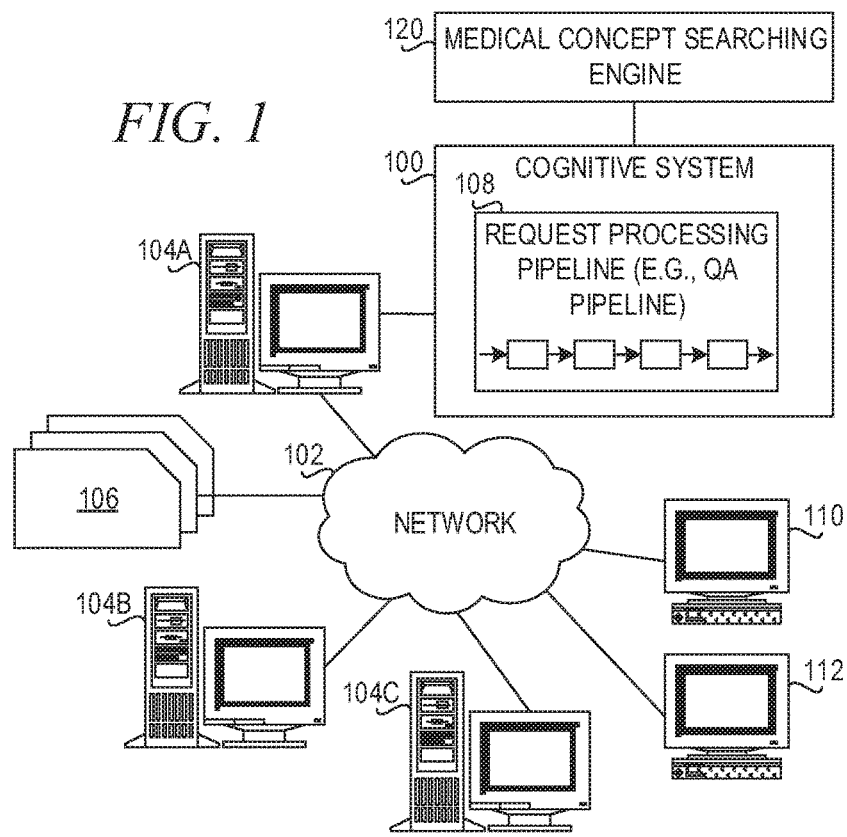
FIG. 1 depicts a schematic diagram of one illustrative embodiment of a cognitive healthcare system in a computer network.

Many life scientists tend to utilize complex combinations of search criteria to pinpoint information of interest to their purposes. However, it becomes difficult for search engines to handle and parse such searches, and many search engines have a limit on the number of criteria that may be utilized. As a result, individuals must self-limit their search criteria and perform additional filtering of content manually while reviewing the search results. Moreover, individuals are not aware a priori of how particular criteria will affect the search results that are generated. Known indexed search engines do not provide suggestions as to how to refine a search based on a predicted impact on the search results.

The illustrative embodiments provide a mechanism for generating a medical concept model of a corpus at index time, which identifies the number of search results that will be generated in response to a particular search criterium.

This information is then used in response to a search request to provide suggestions as to criteria that may be used to further refine the search results generated in response to the search request. The mechanism indicates the amount of impact on the search results that such search criteria may provide. A visual search mechanism is provided to represent categories of medical concepts corresponding to search criteria as a bubble graph that is user selectable to refine search results. The illustrative embodiments provide suggestions to medical information searchers as to how to further refine searches and obtain search results that are more useful to their particular needs.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general-purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular features or elements present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine-readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
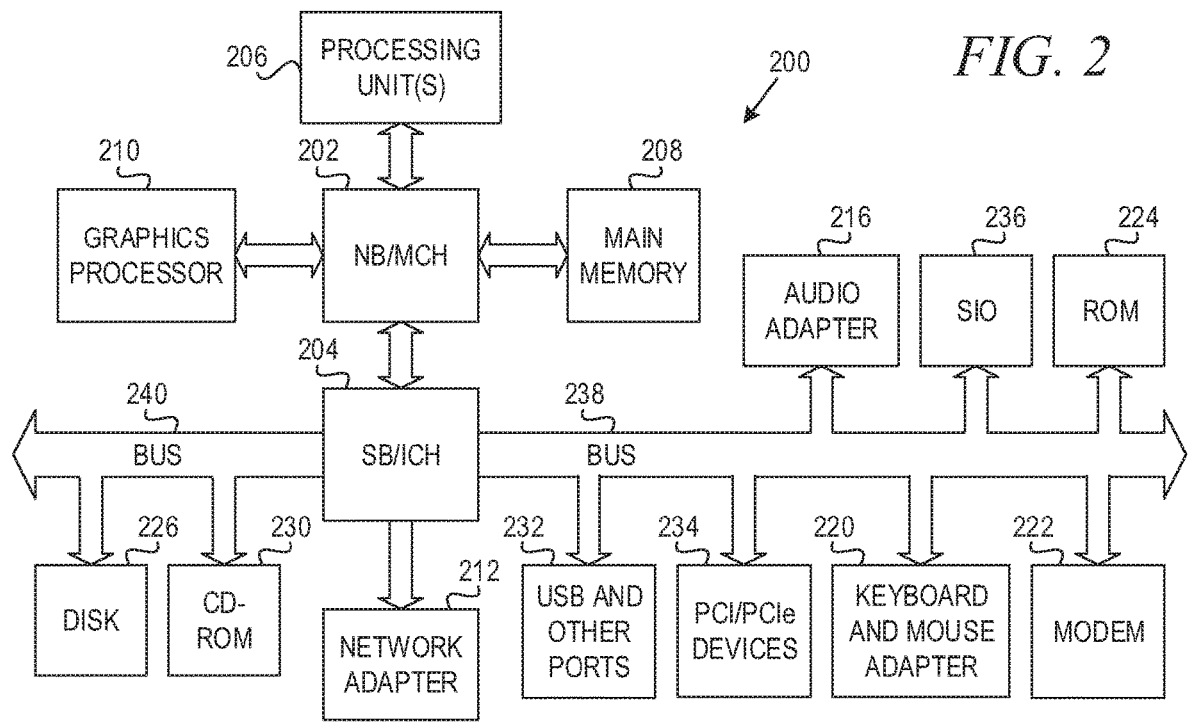
FIG. 2 is a block diagram of an example data processing system in which aspects of the illustrative embodiments are implemented.
Figure 3:
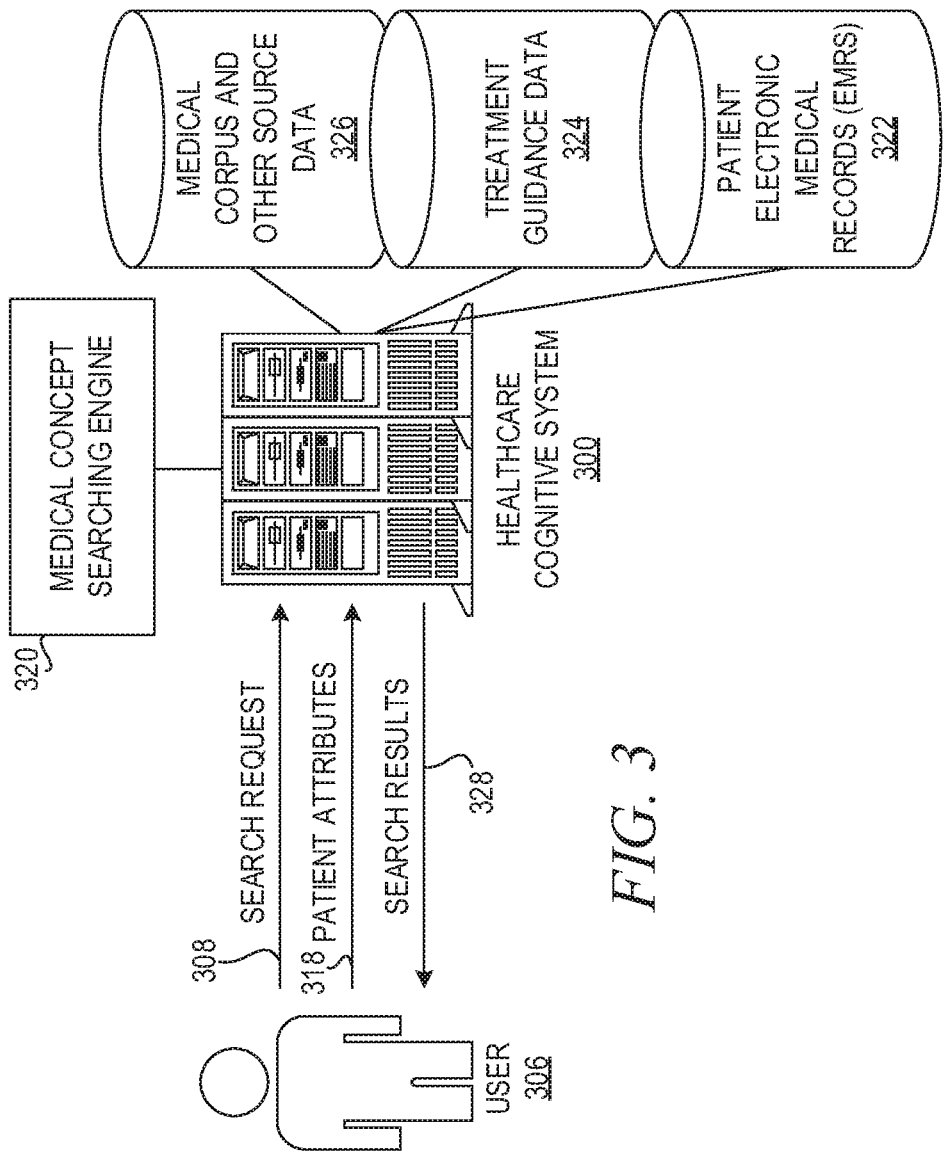
FIG. 3 is an example diagram illustrating an interaction of elements of a healthcare decision support system in accordance with one illustrative embodiment.

As noted above, the present invention provides mechanisms for improving searches of medical concepts based on an index model. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system"), which implements a request processing pipeline, such as a search engine pipeline for example, request processing methodology, and request processing computer program product with which the mechanisms of the illustrative embodiments are implemented. These requests may be provided as structured or unstructured request messages, search requests, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or search criteria in implementations using a search engine), depending on the desired implementation. Moreover, each request processing pipeline may have its own associated corpus or corpora that it ingests and operates on, e.g., one corpus for blood disease domain documents and another corpus for cancer diagnostics domain related documents in the above examples.

As will be discussed in greater detail hereafter, the illustrative embodiments may be integrated in, augment, and extend the functionality of the healthcare cognitive system with regard to improving searches of medical concepts based on an index model. Thus, it is important to first have an understanding of how the cognitive system is implemented before describing how the mechanisms of the illustrative embodiments are integrated in and augment such cognitive systems and request processing pipeline mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 may provide cognitive operations including, but not limited to, request processing and cognitive response generation, which may take many different forms depending upon the desired implementation, e.g., cognitive information retrieval, training/instruction of users, cognitive evaluation of data, or the like. Other embodiments of the cognitive system 100 may be used with components, systems, subsystems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the requests are formed using natural language. The cognitive system 100 parses and interprets the request via a pipeline 108, and provides a response to the cognitive system user, e.g., cognitive system user 110, containing one or more responses to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses.

The cognitive system 100 implements the pipeline 108, which comprises a plurality of stages for processing an input request based on information obtained from the corpus or corpora of data 106. The pipeline 108 generates responses for the input question or request based on the processing of the input request and the corpus or corpora of data 106.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process may be repeated for each of the candidate responses to generate a ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare-based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for medical concept searching engine 120 for improving searches of medical concepts based on an index model. With the mechanism of the illustrative embodiment, at index time, a medical concept index model is generated that identifies the number of search results that will be generated in response to particular search criteria, e.g., terms, phrases, and the like. For example, during indexing of a corpus of documents, the medical concept searching engine 120 records the number of instances of each recognizable medical concept in the documents of the corpus. The medical concept searching engine 120 uses this number to predict the number of search results that would be returned if that medical concept were entered as part of the search criteria of a search request or query. This may be done as well with combinations of medical concepts such that the medical concept searching engine 120 generates a medical concept index model. The medical concept searching engine 120 may define the recognizable medical concepts in terms of a predefined ontology in which medical concepts and may identify their relationships with other medical concepts.

Thereafter, when a user enters a search in which at least one of the search terms is a medical concept recognized by the system, the medical concept searching engine 120 looks to the medical concept index model to identify a medical concept and related medical concepts to suggest potential refinements to the search request or query. That is, the medical concept searching engine 120 may retrieve the medical concepts related to the medical concept specified in the search query. The medical concept searching engine 120 may obtain the corresponding number of search results of the medical concept and the related medical concepts from the medical concept index model. The medical concept searching engine 120 evaluates combinations of medical concepts to determine the impact of adding the related medical concepts to the search query and thereby predict the impact of adding the related medical concepts to the search results. The medical concept searching engine 120 generates a bubble graph representation of this impact where the bubbles of the bubble graph have sizes representing the predicted impact on the search results. These bubbles are selectable by the user to thereby automatically add the related medical concepts to the search query and refine the search results.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements a cognitive system 100 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare decision support system in accordance with one illustrative embodiment. The example diagram of FIG. 3 depicts an implementation of a healthcare decision support system 300 that is configured to provide a summary of EMR data for patients. However, it should be appreciated that this is only an example implementation and other healthcare operations may be implemented in other embodiments of the healthcare decision support system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare decision support system 300 will be electronic via a user computing device (not shown), such as a client computing device 110 or 112 in FIG. 1, communicating with the healthcare decision support system 300 via one or more data communication links and potentially one or more data networks.

As shown in FIG. 3, in accordance with one illustrative embodiment, the user 306 submits a search request 308 to the healthcare decision support system 300, such as via a user interface on a client computing device that is configured to allow users to submit requests to the healthcare decision support system 300 in a format that the healthcare decision support system 300 can parse and process. The search request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient.

The healthcare decision support system 300 provides an AI system that is specifically configured to perform an implementation specific healthcare oriented cognitive operation. In the depicted example, this healthcare oriented cognitive operation is directed to providing search results 328 to the user 306 to assist the user 306 in treating the patient based on their reported symptoms and other information gathered about the patient. The healthcare decision support system 300 operates on the search request 308 and patient attributes 318 utilizing information gathered from the medical corpus and other source data 326, treatment guidance data 324, and the patient EMRs 322 associated with the patient to generate search results 328. In one embodiment, patient EMR data 322 may include biomedical images.

In accordance with the illustrative embodiments herein, the healthcare cognitive system 300 is augmented to include medical concept searching engine 320 for generating search results 328 of medical concepts based on an index model. Medical concept searching engine 320 identifies medical concepts in search request 308, identifies medical concepts related to the identified medical concepts, and generates a bubble graph where each bubble represents a medical concept or related medical concept, where a size of each bubble represents a predicted impact on search results 328 and where each bubble is selectable to add the corresponding medical concept to the search request 308.

Figure 4A:
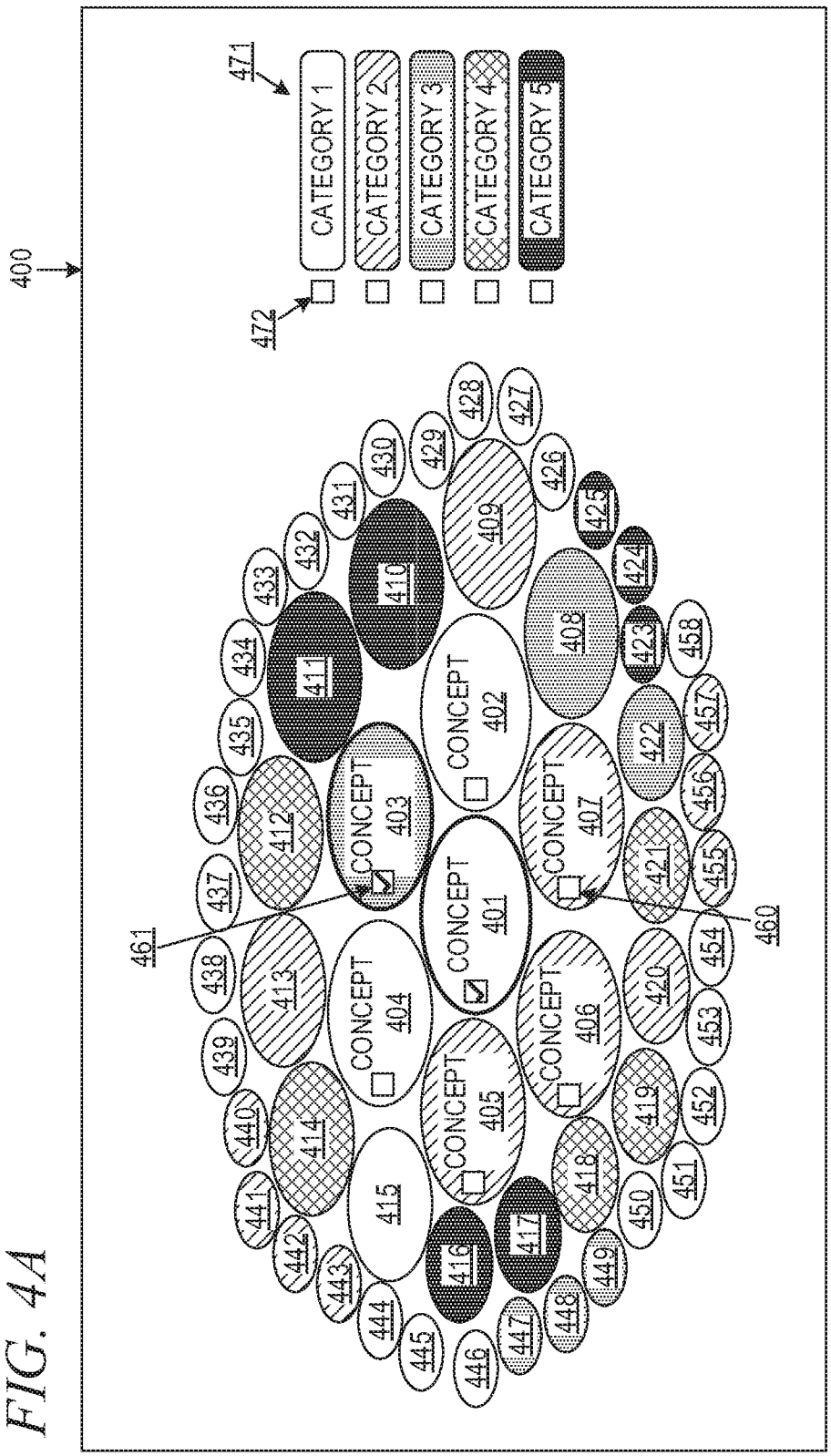
FIGS. 4A and 4B depict example bubble graph for searches of concepts based on an index model in accordance with an illustrative embodiment.
Figure 4B:
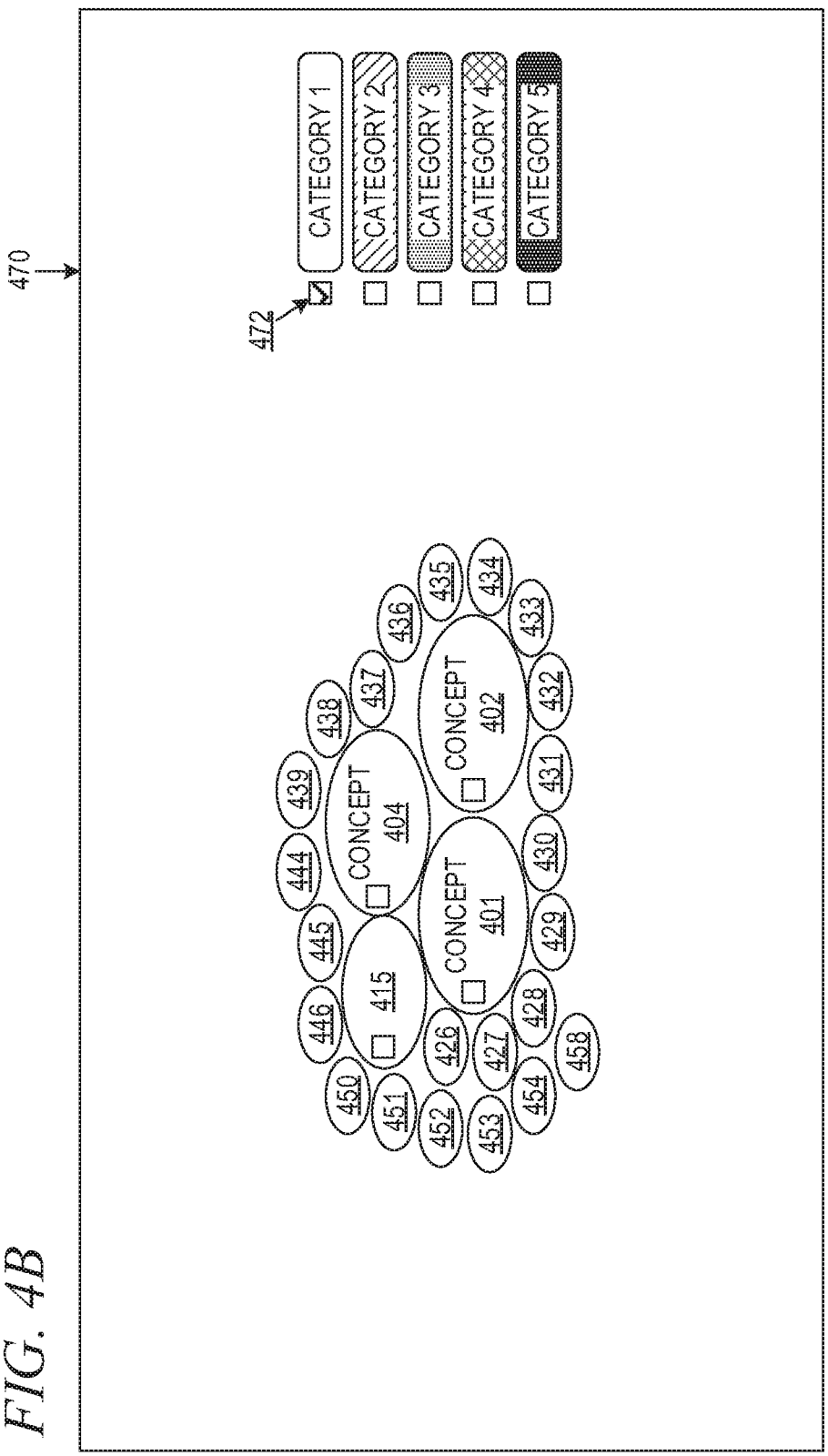

FIGS. 4A and 4B depict example bubble graph for searches of concepts based on an index model in accordance with an illustrative embodiment. With reference to FIG. 4A, bubble graph 400 presents concept bubbles 401-458, each representing a particular concept that may be used to search a corpus of documents. The size of each bubble 401-458 represents a predicted impact on search results. In one example embodiment, a larger bubble represents a concept that would result in more documents in the search results while a smaller bubble represents a concept that would result in fewer documents in the search results. In another example embodiment, a larger bubble represents a concept that would result in more instances of the concept in the search results while a smaller bubble represents a concept that would result in fewer instances of the concept in the search results.

In the depicted example, each bubble includes a selection control 460 that allows the user to select a concept to be included in the search request. For example, selection control 461 indicates that the user has selected concept bubble 403 to be included in the search request. In example shown in FIG. 4A, the selection control is a checkbox; however, other selection controls could be used within the scope of the illustrative embodiment.

In one example embodiment, bubble graph 400 presents at least one concept from the search request, such as concept 401. In this example, the remainder of bubbles 402-458 are concepts found to be related to concept 401 in an ontology. The user may then select related concepts to include in the search request to refine the search.

In an example embodiment, bubbles 401-458 have associated categories 471. For instance, concepts 401, 402, 404, 415, 426-439, 444-446, 450-454, and 458 are of category 1; concepts 405, 406, 407, 409, 413, 420, 440-443, and 455-457 are of category 2; concepts 403, 408, 422, and 447-449 are of category 3; concepts 412, 414, 418, 419, and 421 are of category 4; and, concepts 410, 411, 416, 417, and 423-425 are of category 5. As shown in FIG. 4A, each category has a selection control 472.

FIG. 4B depicts a bubble graph 470 that results from selecting the selection control for category 1. Bubble graph 470 filters the concepts based on the selected categories. In the depicted example, category 1 is selected and concepts 401, 402, 404, 415, 426-439, 444-446, 450-454, and 458 are presented. Thus, the bubble graph user interface allows the user to filter by category and select particular concepts to add to the search request.

Figure 5:
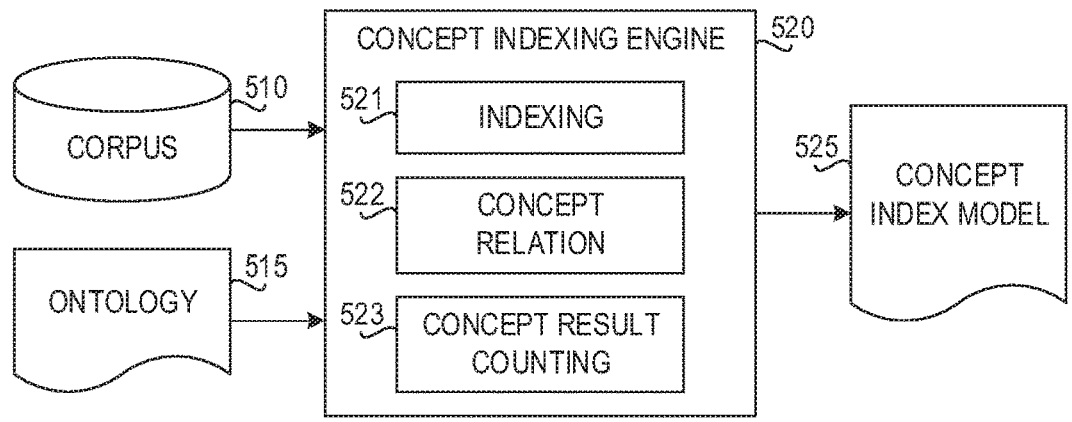
FIG. 5 is a block diagram illustrating a concept indexing engine in accordance with an illustrative embodiment.

FIG. 5 is a block diagram illustrating a concept indexing engine in accordance with an illustrative embodiment. Concept indexing engine 520 comprises indexing component 521, concept relation component 522, and concept result counting component 523. The indexing component 521 indexes corpus 510. Corpus indexing is the process of passing content sources through a set of cognitive analytics that annotator the content with offsets of discovered cognitive artifacts. Each occurrence of a cognitive artifact is recorded per document allowing the corpus index to compute total concentration of the artifact within a corpus and number of content sources the artifact was found in.

Concept relation component 522 matches concepts found in corpus 510 to ontology 515 and identifies relationships between concepts in ontology 515. Concept result counting component 522 calculates a number of documents or a number of instances of each concept and combination of related concepts in corpus 510. The index model computes an aggregation of unique ontology artifacts found in the corpus that outputs the number of documents that contain the artifact. The metric is a union of artifact inclusion counts. When combining an artifact with count A and an artifact with count B the impact can be inferenced by the lowest count, which would be the maximum number of possible results from the selected search criteria.

Concept indexing engine 520 records each concept found in corpus 510 in association with a number of search results that contain the concept, along with combinations of concepts and their corresponding numbers of search results, in concept index model data structure 525.

Figure 6:
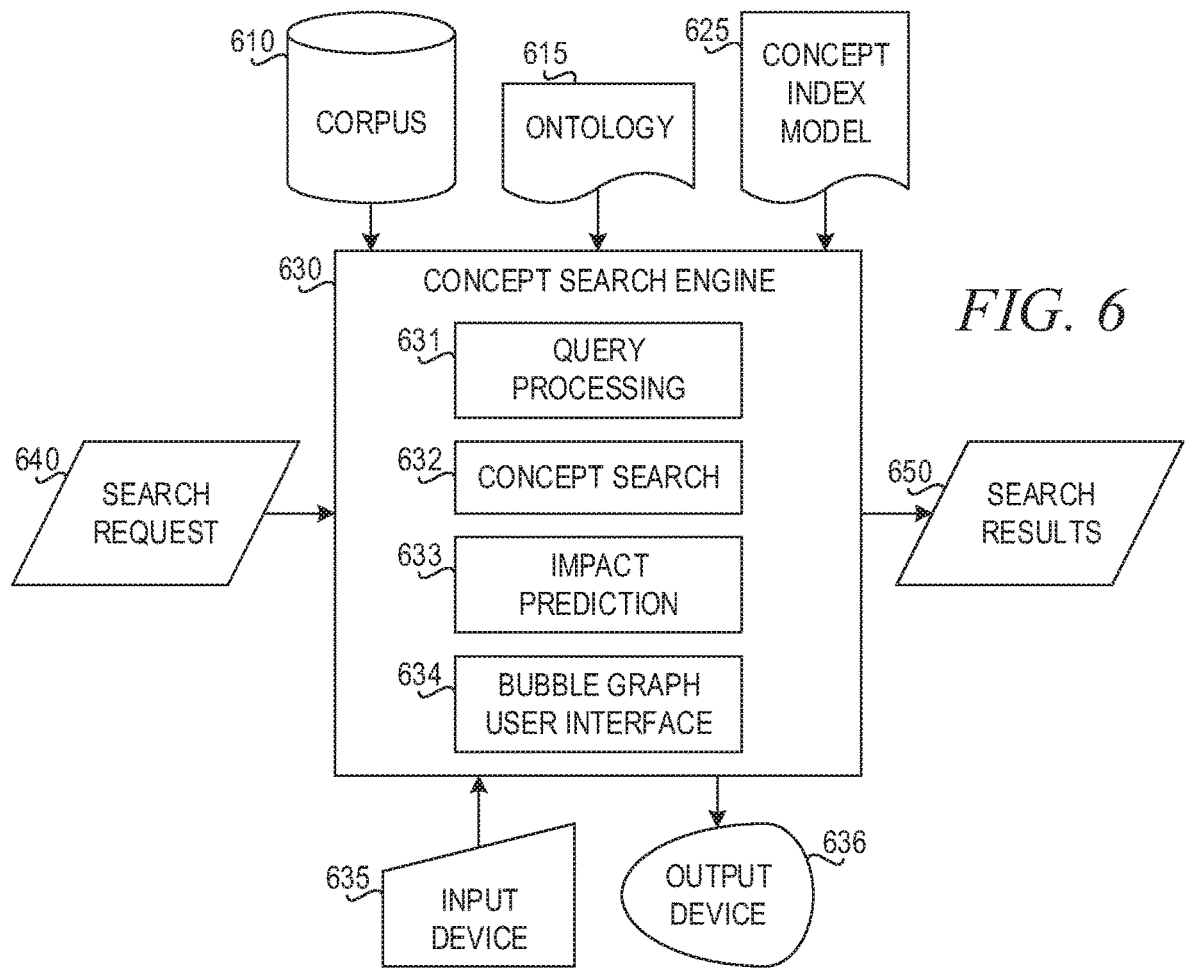
FIG. 6 is a block diagram illustrating a concept search engine in accordance with an illustrative embodiment.

FIG. 6 is a block diagram illustrating a concept search engine in accordance with an illustrative embodiment. Concept search engine 630 comprises query processing component 631, concept search component 632, impact prediction component 633, and bubble graph user interface 634. Concept search engine 630 receives search request 640. Query processing component 631 identifies search criteria, including concepts, in search request 640. Concept search component 632 identifies concepts in the search request 640 and identifies related concepts in ontology 615. Impact prediction component 633 then predicts an impact each concept or combination of concepts has on search results 650.

Bubble graph user interface component 634 generates a bubble graph user interface including the concepts in the search request and related concepts. The bubble graph user interface represents each concept as a bubble having a size proportional to the impact on the search results based on information in concept index model data structure 625. Bubble graph user interface component 634 presents the bubble graph on output device 636 and receives user input via input device 635. The user may filter the concepts by selecting a category, and bubble graph user interface component 634 modifies the bubble graph user interface based on the selected category based on information in concept index model data structure 625. The user may also select bubbles to add particular concepts to the search request 640.

In response to the user selecting a concept via input device 635, concept search engine 630 modifies search request 640 to refine the search. When the user is finished refining the search, concept search engine 630 generates search results 650 to reflect the modified search request 640.

FIG. 7 is a flowchart illustrating operation of a concept indexing engine in accordance with an illustrative embodiment. Operation begins (block 700), and the concept indexing engine identifies a concept in an ontology (block 701). The concept indexing engine determines a number of instances of the concept in the corpus (block 702). The concept indexing engine records the number of instances of the concept in a concept index model (block 703). The concept indexing engine may also record a number of instances of the concept in combination with other concepts in the concept index model.

The concept indexing engine then determines whether the concept is the last concept in the ontology (block 704). If the concept is not the last concept, then operation returns to block 701 to identify the next concept in the ontology. If the concept is the last concept in block 704, then operation ends (block 705).

FIG. 8 is a flowchart illustrating operation of a concept search engine in accordance with an illustrative embodiment. Operation begins (block 800), and the concept search engine receives a search request (block 801). The concept search engine matches the search request to concepts in an ontology (block 802). The concept search engine then generates a bubble graph of the concepts and related concepts with their categories and selection controls that allow the user to filter by category and select concepts for inclusion in the search request (block 803).

The concept search engine determines whether the user selects a category (block 804). If the user selects a category, then the concept search engine filters the bubble graph based on the selected category (block 805).

Thereafter, or if the user does not select a category in block 804, the concept search engine determines whether the user selects a concept in the bubble graph (block 805). If the user selects a concept, then the concept search engine adds the selected concept to the search request (block 807) and refines the search results based on the modified search request (block 808).

Thereafter, or if the user does not select a concept in block 806, the concept search engine determines whether the search refinement by the user is complete (block 809). If concept search refinement is not complete, then operation returns to block 804 to determine whether the user selects a category for filtering the bubble graph. If concept search refine is complete in block 809, then operation ends (block 810).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication-based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a medical concept searching engine for improving searches of medical concepts based on an index model, the method comprising:
   generating a concept index model data structure that records medical concepts and corresponding numbers of instances of the medical concepts in the corpus of documents;
   responsive to receiving a search request from a user, identifying, by the medical concept searching engine, at least one medical concept in the search request;
   identifying, by the medical concept searching engine, one or more related medical concepts that are related to the at least one medical concept based on an ontology data structure;
   determining, by the medical concept searching engine, a predicted impact of each medical concept in the at least one medical concept and the one or more related medical concepts on search results;
   generating, by the medical concept searching engine, a bubble graph user interface comprising a plurality of bubbles corresponding to the at least one medical concept and the one or more related medical concepts, wherein a size of each bubble in the bubble graph user interface is proportional to the predicted impact of the corresponding medical concept on the search results and wherein each bubble in the bubble graph user interface has a selection control that is selectable by the user to add the corresponding medical concept to the search request; and
   presenting, by the medical concept searching engine, the bubble graph user interface to the user.

2. The method of claim 1, Wherein generating the concept index model data structure comprises identifying each given medical concept from an ontology in the corpus of documents; determining a number of instances of the given medical concept in the corpus of documents; and recording the given medical concept in association with the number of instances of the given medical concept in the corpus of documents.

3. The method of claim 2, wherein a larger bubble represents a concept that would result in more instances of the medical concept in the search results while a smaller bubble represents a concept that would result in fewer instances of the medical concept in the search results.

4. The method of claim 1, further comprising responsive to the user selecting a selection control of a given medical concept, adding the given medical concept to the search request.

5. The method of claim 1, wherein the bubble graph user interface comprises a plurality of medical concept categories and wherein each medical concept category has a selection control that allows the user to filter medical concepts by medical concept category.

6. The method of claim 5, further comprising responsive to the user selecting a selection control of a given medical concept category, filtering the bubble graph user interface to include bubbles corresponding to medical concepts of the given medical concept category.

7. The method of claim 5, wherein the plurality of medical concept categories comprise categories of the at least one medical concept and the one or more related medical concepts.

8. The method of claim 1, further comprising generating search results based on the search request and presenting the search results to the user.

9. The method of claim 1, wherein a larger bubble represents a concept that would result in more documents in the search results while a smaller bubble represents a concept that would result in fewer documents in the search results.

10. A computer program product comprising a computer readable storage medium having a computer readable program stored therein, wherein the computer readable program, when executed on a data processing system, causes the data processing system to implement a medical concept searching engine for improving searches of medical concepts based on an index model, wherein the computer readable program causes the data processing system to:
  generate a concept index model data structure that records medical concepts and corresponding numbers of instances of the medical concepts in the corpus of documents;
  responsive to receiving a search request from a user, identify, by the medical concept searching engine, at least one medical concept in the search request;
  identify, by the medical concept searching engine, one or more related medical concepts that are related to the at least one medical concept based on an ontology data structure;
  determine, by the medical concept searching engine, a predicted impact of each medical concept in the at least one medical concept and the one or more related medical concepts on search results;
  generate, by the medical concept searching engine, a bubble graph user interface comprising a plurality of bubbles corresponding to the at least one medical concept and the one or more related medical concepts, wherein a size of each bubble in the bubble graph user interface is proportional to the predicted impact of the corresponding medical concept on the search results and wherein each bubble in the bubble graph user interface has a selection control that is selectable by the user to add the corresponding medical concept to the search request; and
  present, by the medical concept searching engine, the bubble graph user interface to the user.

11. The computer program product of claim 10, wherein generating the concept index model data structure comprises identifying each given medical concept from an ontology in the corpus of documents; determining a number of instances of the given medical concept in the corpus of documents; and recording the given medical concept in association with the number of instances of the given medical concept in the corpus of documents.

12. The computer program product of claim 10, wherein the computer readable program causes the data processing system to add a given medical concept to the search request responsive to the user selecting a selection control of the given medical concept.

13. The computer program product of claim 10, wherein the bubble graph user interface comprises a plurality of medical concept categories and wherein each medical concept category has a selection control that allows the user to filter medical concepts by medical concept category.

14. The computer program product of claim 13, wherein the computer readable program causes the data processing system to filter the bubble graph user interface to include bubbles corresponding to medical concepts of a given medical concept category responsive to the user selecting a selection control of the given medical concept category.

15. The computer program product of claim 10, wherein the computer readable program causes the data processing system to generate search results based on the search request and presenting the search results to the user.

16. A data processing system comprising:
  at least one processor; and
  at least one memory coupled to the at least one processor, wherein the at least one memory comprises instructions which, when executed by the at least one processor, cause the at least one processor to implement a medical concept searching engine for improving searches of medical concepts based on an index model, wherein the instructions cause the processor to:
  generate a concept index model data structure that records medical concepts and corresponding numbers of instances of the medical concepts in the corpus of documents;
  responsive to receiving a search request from a user, identify, by the medical concept searching engine, at least one medical concept in the search request;
  identify, by the medical concept searching engine, one or more related medical concepts that are related to the at least one medical concept based on an ontology data structure;
  determine, by the medical concept searching engine, a predicted impact of each medical concept in the at least one medical concept and the one or more related medical concepts on search results;
  generate, by the medical concept searching engine, a bubble graph user interface comprising a plurality of bubbles corresponding to the at least one medical concept and the one or more related medical concepts, wherein a size of each bubble in the bubble graph user interface is proportional to the predicted impact of the corresponding medical concept on the search results and wherein each bubble in the bubble graph user interface has a selection control that is selectable by the user to add the corresponding medical concept to the search request; and
  present, by the medical concept searching engine, the bubble graph user interface to the user.

17. The data processing system of claim 16, wherein generating the concept index model data structure comprises identifying each given medical concept from an ontology in the corpus of documents; determining a number of instances of the given medical concept in the corpus of documents; and recording the given medical concept in association with the number of instances of the given medical concept in the corpus of documents.

18. The data processing system of claim 16, wherein the instructions cause the processor to add a given medical concept to the search request responsive to the user selecting a selection control of the given medical concept.

19. The data processing system of claim 16, wherein the bubble graph user interface comprises a plurality of medical concept categories and wherein each medical concept category has a selection control that allows the user to filter medical concepts by medical concept category.

20. The data processing system of claim 19, wherein the instructions cause the processor to filter the bubble graph user interface to include bubbles corresponding to medical concepts of a given medical concept category responsive to the user selecting a selection control of the given medical concept category.

* * * * *